United States Patent [19]

Iguchi

[11] Patent Number: 4,972,841
[45] Date of Patent: Nov. 27, 1990

[54] STETHOSCOPE WITH PULSE RATE DISPLAY

[76] Inventor: Robert K. Iguchi, 9116 185th Pl. SW., Edmonds, Wash. 98020

[21] Appl. No.: 270,822

[22] Filed: Nov. 14, 1988

[51] Int. Cl.$^5$ ............................................. A61B 5/0245
[52] U.S. Cl. .................................... 128/715; 128/689
[58] Field of Search ................ 128/715, 773, 687–690, 128/670–671, 672

[56] References Cited

U.S. PATENT DOCUMENTS

| | | |
|---|---|---|
| 3,467,837 | 9/1969 | Vick . |
| 3,921,623 | 11/1975 | Okada . |
| 3,978,848 | 9/1976 | Yen . |
| 4,058,118 | 11/1977 | Stupay . |
| 4,170,717 | 10/1979 | Walshe ................................ 128/715 |
| 4,181,134 | 1/1980 | Mason . |
| 4,220,160 | 9/1980 | Kimball . |
| 4,262,674 | 4/1981 | Uemura . |
| 4,312,358 | 1/1982 | Barney ................................ 128/670 |
| 4,377,727 | 3/1983 | Schwalbach ......................... 128/715 |
| 4,406,290 | 9/1983 | Walbeoffe-Wilson .............. 128/689 |
| 4,436,096 | 3/1984 | Dyck . |
| 4,549,551 | 10/1985 | Dyck . |
| 4,618,986 | 10/1986 | Hower ........................... 128/715 X |
| 4,624,262 | 11/1986 | Berger . |
| 4,679,570 | 7/1987 | Lund et al. .......................... 128/715 |

Primary Examiner—Angela D. Sykes

[57] ABSTRACT

A miniaturized electronic stethoscope designed to be used in conjunction with a standard sphygmomanometer in the measurement of blood pressure and pulse rate simultaneously in which a transducer converts the Korotkoff sounds into electrical signals. The electrical signals are amplified and fed to a counter in which the detected pulse rate per unit time is calculated and then the result is displayed as a digital pulse rate.

11 Claims, 2 Drawing Sheets

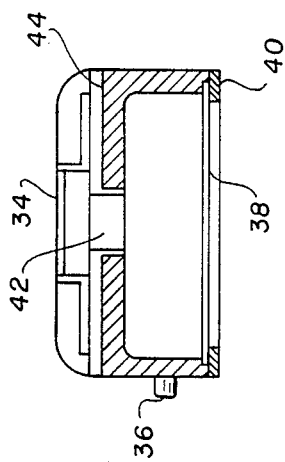
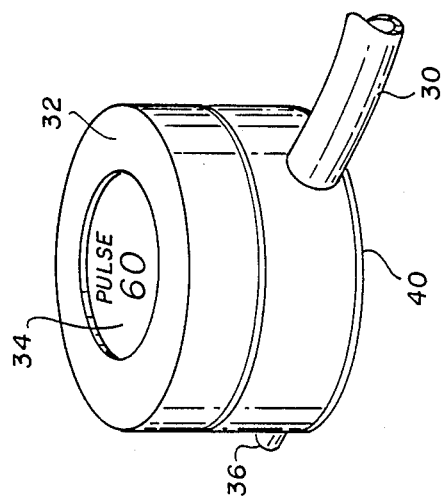
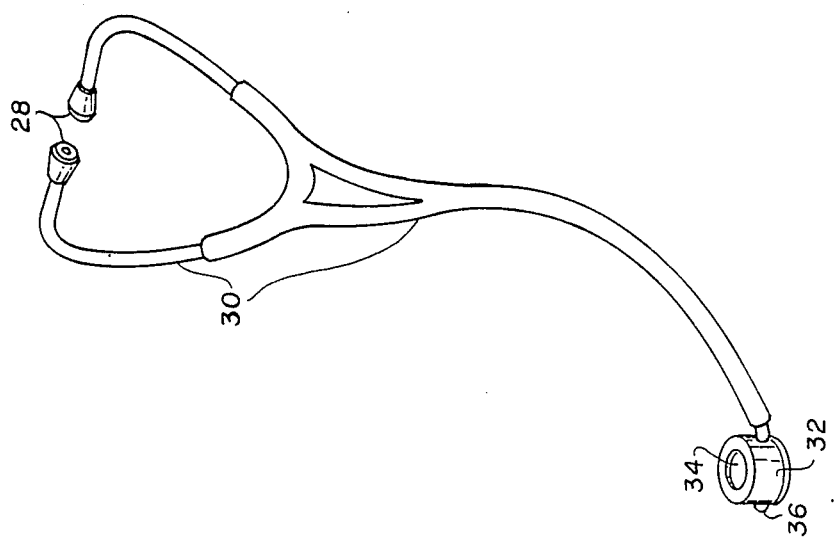

STETHOSCOPE WITH PULSE RATE DISPLAY

BACKGROUND OF THE INVENTION

1. Field of Invention

The present invention relates to a stethoscope which can be used by skilled medical personnel in conjunction with the standard blood pressure sphygmomanometer which would simultaneously measure the pulse rate as the blood pressure is being measured.

2. Description of Prior Art

Nurses, emergency medical technicians, medical assistants, physicians, and other medical personnel frequently require the recording of the vital signs. Every patient encountered in medical offices and outpatient clinics generally require the taking and recording of the vital signs. The major components of said signs include the blood pressure and the pulse rate. Thus, the measurement of the vital signs is an integral part of any medical encounter.

The blood pressure most commonly is obtained with the use of a stethoscope and a sphygmomanometer. The sphygmomanometer consists of an elongated air bladder termed the cuff which is wrapped around an arm of a human patient and air is pumped into said cuff thereby increasing the pressure to a point that the arterial pressure is surpassed and the artery is occluded. The air pressure is then gradually decreased to some level at which Korotkoff sounds (i.e. sounds created by the vibrating collapsed vessel walls as blood is allowed through) can be heard by the use of the diaphragm of a standard stethoscope held directly over the artery. The systolic and diastolic blood pressures are so obtained by auscultating the first and last audible Korotkoff sounds, respectively.

A pulse rate is normally obtained by palpating a peripheral arterial pulse and counting them. This is routinely done by locating and then palpating the radial artery at the wrist, finding a suitable time piece, then counting the number of beats felt over a timed period, usually 10 to 60 seconds, and multiplying that number by the appropriate number to determine the number of pulses per minute. This number is then termed the pulse rate or pulse.

This method is not only time consuming, but may be open to large inherent error. The observer must not be distracted from his count lest he forget the number of beats or the reference mark of the time piece utilized. Medical personnel are often in a hurry and in a setting in which one could be easily distracted. The action of locating the radial artery and waiting for the time piece to come to an appropriate numeral is time wasting.

Heretofore, devices have not utilized the readily available standard blood pressure sphygmomanometer and a stethoscope to also measure the pulse rate simultaneous to the blood pressure measurement. The stethoscope in U.S. Pat. No. 4,436,096 to Dyck, 1984 Mar. 13, responded to heart sounds and since there are two heart sounds per heart beat, the signals were processed in an elaborate manner necessitating a much larger and heavier device and not meant to be used in conjunction with a sphygmomanometer. The apparatus in U.S. Pat. No. 4,624,262 to Berger, does not utilize the Korotkoff sounds and instead uses a dynamometer to respond to arterial pulsations. The apparatus of U.S. Pat. No. 3,978,848 to Yen, et. al., is a more complicated device and is not incorporated into a stethoscope.

Medical personnel are inherently distrustful of any device which does not allow them continued hands on care and which does not rely upon human quality control. Patients also require and demand a certain amount of attention with hands on medical care which multiple electronic devices and high technology have gradually eroded.

Therefore, the need exists for a portable light weight stethoscope which could be used in conjunction with the standard blood pressure cuff to obtain a pulse rate while measuring the blood pressure in a routine fashion.

OBJECTS AND SUMMARY OF THE INVENTION

Accordingly, several objects and advantages of this invention include the ability to simultaneously measure accurately the subject person's pulse rate as the blood pressure is being obtained by standard methods by skilled medical personnel. Devices are available which can measure the patient's blood pressure and give a numeric read out of the pulse rate by other or similar methods. These devices however are impractical for common usage in offices and hospitals because of their expense and bulk and they are not utilized in conjunction with the standard medically accepted methods of blood pressure measurement.

An object of this invention is to measure the heart rate accurately by placing on the stethoscope a device which could respond to the Korotkoff sounds and calCulate an accurate heart rate. This would incorporate two or more actions into one activity o: measuring the blood pressure. The device would then display this data in a numeric fashion somewhere on the stethoscope so it could be recorded. This combination would contribute to the actual medical encounter much more than one would expect.

The invention would include a transducer or microphone for providing an electrical signal in response to the Korotkoff sounds, circuitry to calculate an appropriate corresponding pulse from the time elapsed between the electrical signals over one or more cycles, and a digital display. The invention would be added to a stethoscope and as such would be made of sufficiently light weight materials and design to add very little weIght or bulk to the stethoscope. The stethoscope function otherwise would be unchanged and sounds would not be electronically altered when heard by the observer.

The invention would allow medical personnel the continued hands on patient care that is advantageous to all concerned and allow for human quality control in the case of irregularities of the pulse.

Further objects and advantages of this invention will become apparent from a consideration of the drawings and ensuing description of it.

DESCRIPTION OF DRAWINGS

FIG. 2 is a diagram of the entire stethoscope.

FIG. 3 is a diagram of the stethoscope head and housing.

FIG. 4 is a cross sectional diagram of the stethoscope head and housing.

DETAILED DESCRIPTION OF THE PREFERRED EMBODIMENTS

Figure 1:
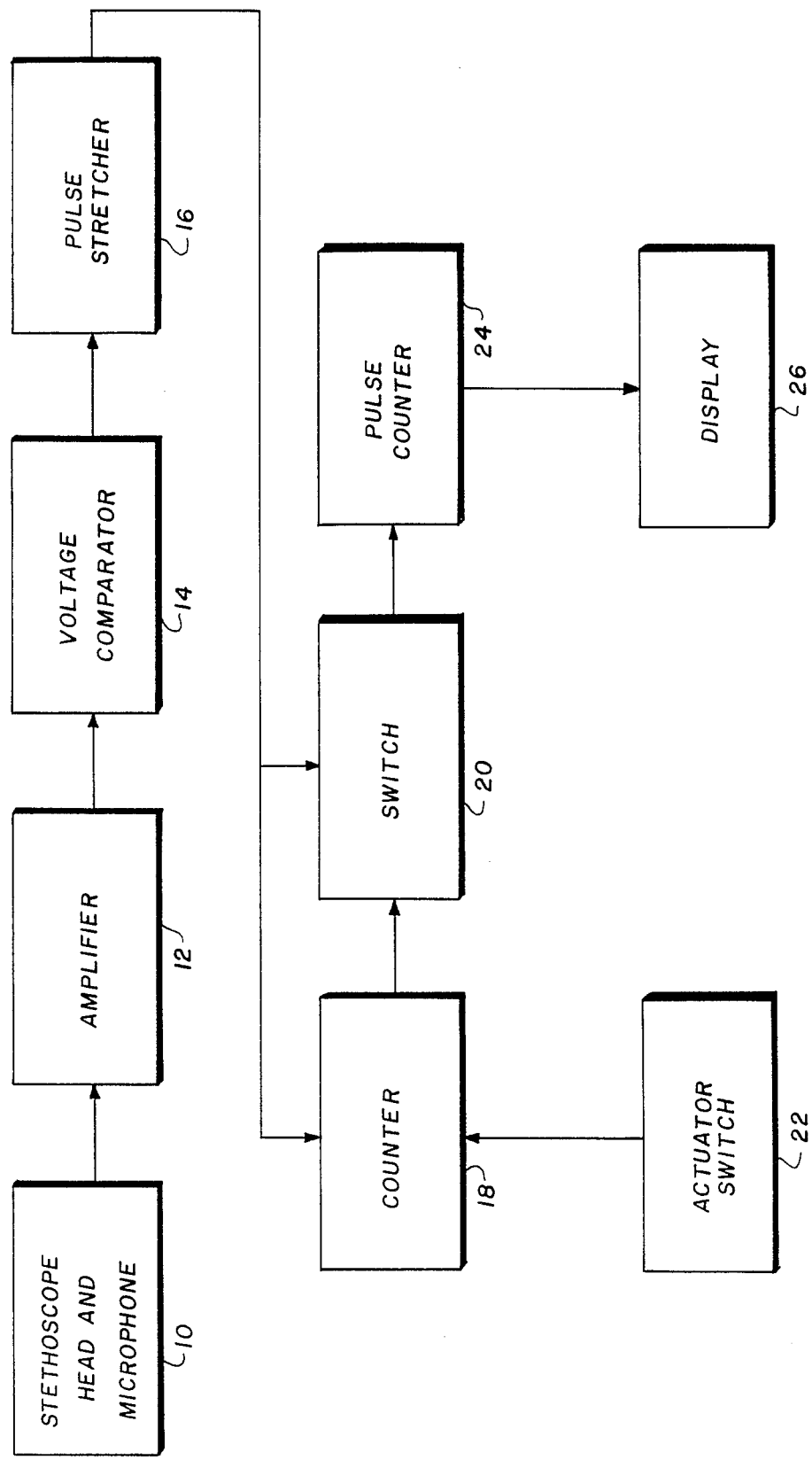
FIG. 1 is a symbolic block diagram of one embodiment of the present invention.

In FIG. 1, Block 10 represents a microphone which is mounted into the head of the stethoscope. The microphone in response to Korotkoff sounds initiates a signal. The microphone in a preferred embodiment would be incorporated into the housing of the head of the stethoscope. The signal is fed into an amplifier, Block 12, which boosts the signal about fifty times. The amplified signal is then input to Block 14, a voltage comparator which compares the signal voltage to a reference voltage. If the signal voltage is greater than the reference voltage, the electrical signal passes. The output of Block 14 is connected to Block 16 which elongates the signal in duration. The output of Block 16 is connected to the inputs of Blocks 18 and 20. The counter in Block 18 sends an off switch signal to Block 20 with each received signal until the operator presses the actuator button Block 22. At this point Block 18 sends an on signal for each received signal to Block 20. The counter in Block 18 allows a set number of such signals to pass until it again turns the switch to the off position. The switch remains off until the start button, Block 22, is pushed again. The pulse counter block, Block 24, calculates the pulse by starting a timer when the first signal is received. The timer is then stopped after the set number of pulses is received and places the resultant elapsed time into the equation X (depending on the set number of signals) divided by the time measured equals the pulse rate per minute. The pulse rate per minute is then sent to a display, Block 26.

In FIG. 2, a preferred embodiment is diagrammed showing the stethoscope head and housing 32 with a digital display 34, preferably an LCD, and an actuator button 36 with flexible tubing 30 and ear pieces 28.

Referring now to FIG. 3, a close up of the stethoscope head and housing 32 is shown with the digital display 34, actuator button 36 in convenient location for one handed usage, diaphragm annulus 40 to secure the diaphragm to the head, and tubing 30.

FIG. 4 is a cross-section of FIG. 3 with the digital display 34, the actuator button 36, diaphragm 38, diaphragm annulus 40, microphone transducer 42, and one or more circuit boards 44 located directly beneath the LCD display.

The operation of the apparatus of the invention will be readily understood from the following description of its use.

Starting with the use of a sphygmomanometer, the observer will inflate the air cuff which has been wrapped about the patient's extremity in the process of taking the blood pressure. The stethoscope head 32 is pressed against the inner aspect of the volar side of the antecubital space where the brachial artery lies as the observer listens with the ear pieces 28 and tubing 30. The air will be slowly released from the air cuff and the Korotkoff sounds will be heard by the observer. With the first loud Korotkoff sound the actuator button 36 will be pushed and the apparatus thus described will respond to the sounds. As the observer completes taking the blood pressure by further release of pressure in the air cuff, the apparatus will read out a pulse so obtained.

Those skilled in the art will recognize that an audible or visual signal of the electrical signal corresponding to the Korotkoff sounds would be advantageous as a means of allowing the observer to become the monitor for judging the accuracy of the device.

Those skilled in the art will also note that it would be advantageous to also have watch functions including a timer, alarm, 24 hour clock functions, and seconds display.

It is obvious for one skilled in the art that numerous modifications may be made to the apparatus of the invention concerning for example the type of stethoscope, the manner of processing the signal, the manner of counting and calculating the results, the manner in which the pulse rate be electronically monitored, without departing from the scope of the invention. A quality control circuit could be added to the invention in which an irregular pulse rate could set off an alarm to notify the observer of this irregularity.

Consequently, the invention should not be interpreted as being limited to the particular embodiment described here, it covers on the contrary all variants thereof.

What is claimed is:

1. An apparatus for rapid and precise external measurement of the pulse rate per unit time comprising:
    a diaphragm with supporting annulus connected to a housing coupled to flexible tubing connected to ear pieces for the auscultation of physiologic functions;
    a transducer for providing an electrical signal in response to sounds or pulses including Korotkoff sounds generated during the process of blood pressure measurement by the use of a sphygmomanometer;
    said transducer coupled to said housing or diaphragm in such a manner that said sounds or pulses produce electrical signals in response to said sounds or pulses;
    computing means by which said electrical signals being generated are processed to generate a pulse rate per unit time;
    means by which said signals are amplified;
    means for displaying said pulse rate;
    an electrical switch allowing the observer to allow said electrical signal to be processed to generate said pulse rate whereby said sounds or pulses are most prominent;
    means by which an abnormal irregular pulse rate be processed in a differing manner thus causing said electrical signal to set off an alarm to alert the observer to the presence of the abnormal irregular pulse rate.

2. Apparatus as claimed in claim 1 and further comprising means for detecting electrical signals exceeding a predetermined threshold level and providing an output signal in response to each amplitude level exceeding said threshold level, said detecting means including a comparator having an input connected to the output of said audio amplifier.

3. Apparatus as claimed in claim 2 and including means for adjusting said threshold level.

4. Apparatus as claimed in claim 2, said threshold level being set for detecting amplitude levels representing the Korotkoff sounds.

5. Apparatus as claimed in claim 1 and including means for providing an audible indication of detected Korotkoff sounds responsive to said electrical signals corresponding to Korotkoff sounds.

6. Apparatus as claimed in claim 1 and including means for selectively modifying the duration of said electrical signals corresponding to said sounds.

7. Apparatus as claimed in claim 1 and including means for providing a visual indication of the detected sounds responsive to said electrical signals corresponding to said sounds.

8. An electronic stethoscope comprising:
- a housing for placement of a flexible membrane stretched across a concavity;
- a ring to affix said membrane to said housing;
- pliable tubing of certain length secured to said housing;
- a microphone for converting sounds including Korotkoff sounds into electrical signals;
- means of coupling said membrane to said microphone;
- means by which amplitude levels of said signals are compared to a predetermined threshold amplitude and any said signals above said threshold be allowed to pass;
- means by which said signals are elongated in duration;
- means by which said signals are processed to generate a pulse rate per unit time;
- means for providing a visual display of said pulse rate;
- means by which said signals are amplified;
- means by which an irregular pulse rate is processed in such a manner that an alarm circuit is triggered to notify the observer of such an abnormality.

9. Apparatus as claimed in claim 8 and further comprising means for providing a visual and audio indication of the detected sounds responsive to said electrical signals.

10. Apparatus as claimed in claim 8 and further including an activator switch by which an observer can activate the said device upon the initial fully audible Korotkoff sound.

11. Apparatus as claimed in claim 8 and further including circuitry to include watch functions including a timer, alarm, and twenty four hour clock settings.

* * * * *